(12) United States Patent
Smiley

(10) Patent No.: US 10,588,313 B1
(45) Date of Patent: Mar. 17, 2020

(54) COMPOUNDS OF FATTY ACIDS AND AMMONIUM FATTY ACID SALTS

(71) Applicant: Falcon Lab, LLC, Wilmington, DE (US)

(72) Inventor: Robert A. Smiley, Wilmington, DE (US)

(73) Assignee: Falcon Lab, LLC, Wilmington, DE (US)

( * ) Notice: Subject to any disclaimer, the term of this patent is extended or adjusted under 35 U.S.C. 154(b) by 0 days.

(21) Appl. No.: 16/584,064

(22) Filed: Sep. 26, 2019

Related U.S. Application Data

(62) Division of application No. 16/241,695, filed on Jan. 7, 2019, now Pat. No. 10,426,163.

(51) Int. Cl.
*A01N 37/02* (2006.01)

(52) U.S. Cl.
CPC .................... *A01N 37/02* (2013.01)

(58) Field of Classification Search
CPC ...................................................... A01N 37/02
See application file for complete search history.

(56) References Cited

U.S. PATENT DOCUMENTS

| | | | | |
|---|---|---|---|---|
| 3,867,300 A * | 2/1975 | Karabinos | ............... | A01N 37/02 514/558 |
| 6,503,869 B1 * | 1/2003 | Beste | ..................... | A01N 37/02 504/127 |
| 2006/0199737 A1 * | 9/2006 | Smiley | .................. | A01N 57/20 504/165 |

* cited by examiner

*Primary Examiner* — Shirley V Gembeh
(74) *Attorney, Agent, or Firm* — John Wilson Jones; Jones Delflache LLP

(57) ABSTRACT

A compound containing one mole of a free fatty acid and one mole of the ammonium salt of the fatty acid and represented by the structural formula (I):

$$CH_3(CH_2)_xCOOH \cdot CH_3(CH_2)_xCOO^-NH_4^+ \quad (I)$$

wherein x is 6, 7 or 8. Bacterial contaminated surfaces may be disinfected or bacteria removed from a bacterial contaminated surface by applying onto the surface a bactericidally effective amount of the compound.

20 Claims, No Drawings

COMPOUNDS OF FATTY ACIDS AND AMMONIUM FATTY ACID SALTS

This application is a divisional of U.S. patent application Ser. No. 16/241,695, filed on Jan. 7, 2019.

FIELD OF THE DISCLOSURE

The disclosure relates to compounds composed of one mole of the ammonium salt of a $C_8$-$C_{10}$ fatty acid hydrogen bonded to one mole of a $C_8$-$C_{10}$ fatty acid. The disclosure further relates to the method of using one or more of the compounds for disinfecting a bacterial contaminated surface and/or the removal of bacteria from a bacterial contaminated surface.

BACKGROUND OF THE DISCLOSURE

It has become apparent in recent years that bacterial infections in hospitals, nursing homes, gyms, animal barns and other places where disease-causing bacteria can survive and spread have risen significantly. Furthermore, many strains of bacteria have become increasingly more resistant to available antibiotics that previously could be used to treat acquired infections. Thus, infections acquired in environments where bacteria thrive are and will continue to be serious health threats.

Efforts to control bacterial infection in places where such illnesses can spread, such as hospitals, are usually centered on destroying the organisms that cause infection with antimicrobial agents known as disinfectants or sanitizers.

Disinfectants, as defined by the Environmental Protection Agency (EPA), are liquid substances that can be sprayed or wiped on hard inanimate surfaces that result in the destruction or irreversible inactivation of infectious fungi and bacteria on the treated surface. Hospital disinfectants are most critical to infection control and are used on medical and dental instruments, floors and walls, bed linens, toilet seats and other surfaces.

Sanitizers are used to reduce, but not necessarily eliminate, the activity of microorganisms from inanimate surfaces to levels considered safe as determined by public health codes or regulations. Sanitizers include food contact products that are used on sites where consumable food products are placed or stored such as dishes and cooking utensils and equipment found in dairies, food processing plants and restaurants.

By late 2013, the EPA had registered about 275 active antimicrobial ingredients. The known antimicrobials can be classified into nine main categories: acids, alcohols, aldehydes, alkalis, biquanides, halogens, oxidizing agents, phenols and quaternary ammonium compounds.

Acidic disinfectants such as acetic acid, citric acid and fatty acids destroy the bonds of nucleic acids and precipitating proteins. Their effectiveness as antimicrobial agents is highly pH dependent, i.e. increased acidity enhances their effectiveness. Concentrated solutions of acids can be corrosive, cause chemical burns, and can be detrimental to the lungs and skin at high concentrations in the air. Fatty acids are less corrosive but can only be used in combination with a soap or surfactant since they are oily substances that are insoluble in water. Fatty acids also have highly offensive odors. These characteristics limit the use of acidic disinfectants.

Alcohols such as ethanol and isopropanol are broad-spectrum antimicrobial agents that damage microbes by denaturing proteins causing membrane damage and cell lysis. To be effective disinfectants, a high concentration, usually 65-90 weight percent, must be used. The activity of alcohols is limited in the presence of organic matter. Furthermore, alcohols are highly flammable, can cause damage to rubber and plastics, and can be very irritating to injured skin.

Aldehydes such as formaldehyde and glutaraldehyde are highly effective, broad-spectrum disinfectants that mainly achieve sterilization by denaturing proteins and disrupting nucleic acids. These substances are highly irritating, toxic to humans and animals on contact or inhalation and are potentially carcinogenic; therefore, their use is limited.

Alkali disinfectants, such as sodium or ammonium hydroxide, work by dissolving lipids within the envelopes of the microorganism. The activity of alkali compounds is slow but can be increased by increasing the treatment temperature. Sodium hydroxide is highly caustic and protective clothing, rubber gloves and safety glasses must be used during application. Ammonium hydroxide is very odorous and the vapors can be injurious to the eyes and lungs. Alkali disinfectants are also not considered to be effective against most bacteria.

Biguanides, as represented by chlorhexidine, kill microorganisms by reacting with the negatively charged groups on cell membranes. They can only function in a limited pH range (5-7) and are easily inactivated by soaps and detergents.

Halogen compounds such as sodium hypochlorite and iodine compounds are broad-spectrum antimicrobials that are inexpensive, readily available and easy to use. They function by denaturing proteins. Sodium hypochlorite can be very caustic, is irritating to the mucous membranes, eyes and skin, is rapidly deactivated by light and some metals, loses effectiveness in the presence of other organic matter and has poor residual activity. Iodine agents have the same advantages and disadvantages as sodium hypochlorite and are deactivated by quaternary ammonium compounds and especially organic debris.

Oxidizing agents such as hydrogen peroxide and peracetic acid function by denaturing the proteins and lipids of microorganisms. In their diluted form, these agents are relatively safe but may be irritating and damage clothing when concentrated. Some metals, e.g. iron, rapidly deactivate them. They also lose effectiveness when there is organic debris present.

Phenols (pine oils) are broad-spectrum disinfectants that function by denaturing proteins and inactivating membrane-bound enzymes to alter the cell wall permeability of microorganisms. Phenols are usually applied as water emulsions with soap or detergents since they have low solubility in water. Concentrations of 5% are most effective but they are not effective against microorganism spores. Prolonged exposure to the skin may cause irritation. Concentrations over 2% are highly toxic to all animals, especially cats.

Quaternary ammonium compounds, referred to as "quats" or QACs, are cationic detergents that are attracted to negatively charged surfaces of microorganisms where they irreversibly bind phospholipids in the cell membrane and denature proteins, thus impairing permeability. They are most active at neutral to slightly alkaline pH but lose their activity at a pH less than 3.5. Organic matter, detergents, soaps and hard water readily inactivate quats.

Each of the disinfectants referenced above has serious shortcomings that limit their use. Some are hazardous to apply and none of them are effective in all situations. While most of these disinfectants have been known for decades, there have been very few antimicrobials discovered in recent years.

In J. V. Karabinos and H. J. Ferlin, *The Journal of the American Oil Chemists' Society*, June 1954, Volume 31, Issue 6, pp 228-232, the antimicrobial activity of fatty acids in the $C_9$ to $C_{12}$ range in dilute acetic acid were examined. The authors concluded that the more acidic the solution, the higher the antibacterial effectiveness. In an article entitled Antimicrobial Agents Derived from Fatty Acids by J. J. Kabara, *The Journal of the American Oil Chemists' Society*, vol. 61, no. 2, pp. 397-403 (1984), the author screened even numbered fatty acids from $C_8$ to $C_{18}$ (both saturated and unsaturated) for antimicrobial activity against four different bacteria. He found no activity toward *Pseudomonas aeruginiosa* while the $C_{10}$ acid (capric acid) gave the highest activity against *Streptococcus* Group A, *Staphlycoccus aureous* and *Candida albicans* of any of the fatty acids tested. The only fatty acid derivatives studied were esters.

U.S. Pat. No. 3,867,300 also discloses antimicrobial activity of fatty acids in water in the presence of non-ionic or anionic detergents at an optimal pH of 6 to 8. U.S. Pat. No. 4,404,040 describes short-chain fatty acid compositions with sanitizer solutions in the pH range of 2.0 to 5.0. U.S. Pat. No. 5,330,769 disclose the use of mixtures of nonanoic and decanoic acids ($C_9$ and $C_{10}$ fatty acids) in strong acids as sanitizers sufficient to lower the pH of the final solutions to 1 to 5. In addition to low pH, these references require water solubilizers or emulsifiers in the formulations with the fatty acids in order to allow the acids to be dispensed in water.

Accordingly, there is a need for alternative disinfectants effective against microorganisms, are safe to use without protective gear (other than eye protection) during their use, are non-toxic to humans or animals by ingestion or absorption through the skin and are relatively low cost.

SUMMARY OF THE DISCLOSURE

In an embodiment, a stable, non-hygroscopic solid compound is provided, the compound having the structural formula (I):

$$CH_3(CH_2)_xCOOH.CH_3(CH_2)_xCOO^-NH_4^+ \qquad (I)$$

wherein x is from 6 to 8.

In another embodiment, a disinfectant composition is provided, the disinfectant composition comprising a rheopectic aqueous composition containing at least one compound of the structural formula (I):

$$CH_3(CH_2)_xCOOH.CH_3(CH_2)_xCOO^-NH_4^+ \qquad (I)$$

wherein x is from 6 to 8.

In another embodiment, a method of disinfecting a bacterial contaminated surface is provided, the method comprising applying onto the surface a bactericidally effective amount of at least one compound of the structural formula (I):

$$CH_3(CH_2)_xCOOH.CH_3(CH_2)_xCOO^-NH_4^+ \qquad (I)$$

wherein x is from 6 to 8.

In another embodiment, a method of removing bacteria from a bacterial contaminated surface is provided, the method comprising applying onto the surface a bactericidally effective amount of at least one ammonium compound represented by the stable, non-hygroscopic solid compound of the structural formula (I):

$$CH_3(CH_2)_xCOOH.CH_3(CH_2)_xCOO^-NH_4^+ \qquad (I)$$

wherein x is from 6 to 8.

In yet another embodiment, a method of disinfecting a bacterial contaminated surface is provided, the method comprising applying onto the surface a bactericidally effective amount of a compound of the structural formula (I):

$$CH_3(CH_2)_7COOH.CH_3(CH_2)_7COO^-NH_4^+ \qquad (I).$$

DETAILED DESCRIPTION OF THE PREFERRED EMBODIMENTS

The water dispersible compounds defined herein consist of one mole of a free $C_8$-$C_{10}$ fatty acid hydrogen bonded to one mole of the ammonium salt of a $C_8$-$C_{10}$ fatty acid. In an embodiment, the compounds may be composed of one mole of a saturated straight chain $C_8$-$C_{10}$ fatty acid and one mole of the ammonium salt of a saturated straight chain $C_8$-$C_{10}$ fatty acid. The straight chain fatty acid of the ammonium salt in a preferred embodiment is the same as the saturated straight chain fatty acid. The chemical names of the saturated straight chain fatty acids include octanoic acid, nonanoic acid and decanoic acid.

The structural formula of the compounds may be represented by (I):

$$CH_3(CH_2)_xCOOH.CH_3(CH_2)_xCOO^-NH_4^+ \qquad (I)$$

wherein x is 6, 7, or 8. These formulae are based on NMR, GCMS, FTIR and elemental analyses. The proton NMR analysis indicates one ammonium ion and two aliphatic carbon chains. The GCMS identifies the presence of the starting acid.

The compounds in the pure state are soft, waxy, white solids with sharp melting points. The compounds are very stable, insoluble but dispersible in water, non-hygroscopic, microcrystalline solids.

The solid products obtained are completely stable when exposed to the atmosphere, i.e., they do not absorb water or carbon dioxide from the air. The compounds are believed to form as the result of hydrogen bonding wherein a hydrogen atom covalently bonded to nitrogen becomes attracted to the oxygen of the carboxylic acid forming a hydrogen bond.

Since the compounds are stable at ambient temperatures and pressures and exist as non-hygroscopic crystalline solids, they may be transported as 100% active ingredients to their point of use. The solid compounds do not decompose on long-term storage. The compounds can be stored and shipped in any type of container, including plastic, paper or cloth bags, metal, glass or plastic. In an embodiment, the compounds can be transported in such containers to the point of use by mixing with water to produce disinfecting compositions.

The compounds may be made by the room temperature evaporation of water from solutions of the ammonium salts of fatty acids until a constant weight of solid residue is obtained. Water dispersions of these compounds can be made by adding the solid compound into water with agitation. This produces an aqueous composition of the compound, the pH of the composition being about 8. The water of the aqueous composition is then evaporated until there is no more weight loss. The residue is a water-free solid compound with a sharp melting point that chemical analyses confirm is the compound described.

In an embodiment, the compounds may be prepared by first reacting one or more moles of a short chain (saturated $C_8$-$C_{10}$ straight chain aliphatic fatty acids) with an equivalent number of moles of aqueous ammonia to form a solution of the ammonium salt of the fatty acid. The pH of the solution after reaction of the fatty acid and ammonia is about 8.0 or higher. The water of the solution is then allowed to evaporate to the atmosphere at atmospheric pressure or under vacuum in a suitable receptacle that includes trays, such as those made of glass, plastic or stainless steel. Heat or vacuum may be applied to hasten evaporation or air may be blown across the solution in the open receptacle. As the water evaporates, the solution becomes thick (grease-like) and the pH of the salt solution slowly decreases to about 7.0 or lower by the loss of a mole of ammonia. Further drying results in the anhydrous solid compound.

In another embodiment, the compounds may be prepared by adding two moles of the fatty acid to a mole of aqueous ammonia. A thick gel results. The gel is transferred to a suitable tray and exposed to the atmosphere until the dry solid complex is formed as indicated by a constant weight or other means. The process may be hastened by applying heat or vacuum to the tray containing the gel or by blowing air across it from a fan. The compounds function as disinfectants when applied onto surfaces contaminated with bacteria. In this embodiment, a bactericidally effective amount of a complex of formula (I) may be applied onto the contaminated surface. In an embodiment, bacteria may be removed from a bacterial contaminated surface when a bactericidally effective amount of the complex of (I) is applied onto the contaminated surface.

In an embodiment, the surface onto which the complex of structure (I) is applied is contaminated with a gram negative bacteria or a gram positive bacteria. The compound(s) is typically applied to the bacterial contaminated surface in an aqueous formulation. One or more of the compounds may be present in the aqueous formulation.

When the solid compound is mixed with water, it completely distributes in the water to produce a uniform composition in the absence of any emulsifier, surfactant, soap, wetting agent, dispersing agent or suspending agent. The solid compound, while being water-insoluble, remains stable as a dispersion indefinitely.

In an embodiment, the dispersion may be prepared by adding a molar amount of a $C_7$-$C_{10}$ fatty acid to an aqueous solution containing an equimolar amount of the ammonium salt of the same $C_7$-$C_{10}$ fatty acid. The dispersion may be prepared without the use of an emulsifier, surfactant, soap, wetting agent, dispersing agent or suspending agent.

Compositions containing the compound are rheopectic. Rheopecty is a rare property of non-Newtonian fluids wherein the viscosity of the fluid increases when the fluid is subjected to shearing forces, such as agitation (for instance, by stirring, shaking or other mechanical agitation). The rheopectic property of the composition becomes visually apparent when the composition is stirred or shaken.

The aqueous formulation applied to the bacterial contaminated surface typically contains between from about 0.1 to about 6, preferably between about 0.5 to about 5, weight percent of the compound(s). In a preferred embodiment, the aqueous formulation contains between from about 1 to about 4, more preferably from about 1 to about 2 weight percent of the compound(s).

The pH of the formulation is usually 6 or above.

In a preferred embodiment, the solid compound(s), at the point of use, may be mixed with water at the desired concentration to render the homogeneous stable emulsion.

The soap-like, opaque water dispersion is non-flammable and has little or no odor during application. Furthermore, the aqueous composition before spraying is water-like in viscosity. It may increase in viscosity on agitation during spray application due to rheopectic properties of the dispersions that may increase the adherence of the active ingredient to surfaces being disinfected. Increase in viscosity during agitation is further attributable to induced stresses by normal motion of the sprayer as well as by the composition passing through the spray head under pressure. The increased thickening of the composition upon agitation decreases drift of the composition away from the targeted surface during spraying. As such, the rheopectic nature of the fluid limits exposure of the fluid from a conventional sprayer to non-targeted surface by curtailing overspray. The rheopectic property of the composition further increases the adherence of the spray to the surface of the bacteria.

The aqueous composition containing the complex is odorless. Thus, during spraying, the end user is not subjected to any unpleasant odor.

As described, bacteria may be removed from a bacterial contaminated surface by applying onto the contaminated surface a bactericidally effective amount of the complex(es). Water dispersions of these compounds kill or deactivate microorganisms almost immediately on contact, for example, on human or animal skin, food preparation surfaces, health care facility surfaces or any other surface that needs or requires the killing or deactivation of microorganisms. The complex(es) is particularly effective in the removal of bacteria on surface of vegetables and other crops. They are particularly effective in removing *Enterococcus faecalis*, *Escherichia coli* and *Salmonella enterica* which present threats to vegetables, including lettuce and mushrooms. The fatty acid ammonium salts may be applied before harvesting or during harvesting.

The complexes defined herein are especially effective in surfaces contaminated with gram negative bacteria as well as surfaces contaminated with gram positive bacteria. In an embodiment, the salts are particularly effective in disinfecting surfaces contaminated with *Pseudomonas aeruginiosa*, *Streptococcus* Group A, *Staphlycoccus aureous*, *Staphylococcus epidermidis*, *Serratia marcescens*, *Enterococcus faecalis*, *Salmonella enterica*, *Escherichia coli*, methicillen resistant *Staphlycoccus aureous* (MERS) or *Candida albicans* or a combination thereof.

The antimicrobial agents defined herein are derived from renewable sources (i.e., they satisfy governmental requirements to be designated organic). As stated, the complexes may be made from ammonia and short chain fatty acids (C8-C10 straight-chain aliphatic acids) which are prevalent in nature as well as being found in both animal and vegetable fats.

For instance, nonanoic acid is present in fruits. For example, it is present in apples, the skin of grapes and in grape pulp. It volatilizes from leaf surfaces of many plants (washes onto soil from rain), certain flowers and the biodegradation of fats. It has been quantitatively detected in drinking water, rain water and snow as well as in air, groundwater and dust. It is a volatile component of raw beef and has been detected in fresh mussels. Ammonia in the environment is a part of the nitrogen cycle and is gaseous decomposition products of animal waste. The principal form of ammonia in the atmosphere is as $NH_3$ (a gas), not as the ammonium ion, $NH_4^+$, which is not gaseous and exists only in water.

The complexes are also effective in destroying fungus.

All percentages set forth in the Examples are given in terms of weight units except as may otherwise be indicated.

EXAMPLES

Example 1

At room temperature and with stirring, 316 g (2 mol.) of technical grade nonanoic acid were added to 125 g of commercial 28-30% aqueous ammonia (approx. 2 moles of ammonia). The temperature increased 24° C. from ambient temperature due to the heat of neutralization. A slurry of white solid formed immediately. About 200 ml of distilled water were added with stirring to obtain a clear solution with a pH of 8. The solution was poured into a weighed plastic tray exposed to the atmosphere at room temperature on a triple beam balance. Periodic weights were observed to measure any loss in weight due to evaporation. White solid formed by the end of day one as the weight of the tray decreased. Eventually a thick grease-like gel formed that slowly turned into a powdery solid as the weight of the tray continued to decrease. The pH of the tray contents at the gel stage was 7. After the weight of the tray and contents remained unchanged and the weight stayed constant for over 3 days, the amount of solid in the tray was 325.0 gm. The solid was water insoluble but could be dispersed in water to form a uniform, opaque, milk-like mixture with a pH of 6. Such dispersions remained unchanged in appearance after months of storage. The solid was very soluble in methanol, ethanol and DMSO, slightly soluble in acetone and insoluble in acetonitrile and ethyl acetate at room temperature. It melted sharply at 62° C.

The proton NMR showed a broad signal for the ammonium protons at about 7.4 ppm. The integration for this $NH_4^+$ peak is about a 1:1 ratio to the alpha $CH_2$ triplet of the carboxylate at 2.1 ppm. That indicates that there is one ammonium ion per two alkyl chains. GC-mass spectral analysis confirmed that the solid contained nonanoic acid. The FT,IR spectrum did not match any spectra available in published infrared spectra files. The average elemental analyses of duplicate samples were 4.18% nitrogen, 12.16% hydrogen and 64.33% carbon. This corresponds to a chemical formula of $C_{18}H_{39}O_4N$ with calculated values of 4.20% N, 11.71% H and 64.86% C, indicating that the isolated solid contained two molecules of nonanoic acid and one molecule of ammonia. The 325 g of isolated product represented a yield of 97.6% of the X=7 compound that can be named ammonium di-nonanoate. All efforts, including two university laboratories, to grow a crystal of this compound for x-ray diffraction studies failed suggesting that the compound is a liquid crystal.

Example 2

A 10% dispersion of the solid compound described in Example 1 was made by adding 10 gm. of the white powder with stirring to 90 gm. of distilled water in a 4 ounce clear glass bottle. After standing for 4 hours, a white, opaque, uniform thin liquid was obtained. The pH of the liquid was 6. The bottle was then shaken vigorously for several minutes. The contents of the bottle changed to a foamy, motionless, thick gel that totally filled the bottle. After standing overnight, the gel remained the same, still filling the bottle. But after standing for 48 hours, the gel reverted to the original thin liquid. Upon shaking the bottle again, the thick gel reappeared. This demonstration of the rheopectic properties of dispersions of the compound described in Example 1 was repeated many times with the same result each time.

Example 3

A 1:99 mixture of the solid compound described in Experiment 1 was made by adding 0.2 gm. to 19.8 ml. of sterile water. Following ASTM International Method E2315 for assessment of antibacterial activity, 10 ml of this uniform mixture was aliquoted into a sterile vessel to produce a 1% dispersion that was then inoculated with the Gram-positive bacterium *Staphylococcus aureus* ATCC 6538 at 25° C. for a target concentration of $1 \times 10^6$ CFU (cells)/ml. One ml of the inoculated substance was harvested at each contact time and neutralized in 9 ml of D/E broth. Enumerations were performed for each time point using standard microbiologic plating methods. At time zero, the percent reduction in bacteria was already 99.9997%, the limit of detection. The percent reduction at 30 seconds, 2 minutes and 10 minutes were also 99.9997%. When 0.1 ml of the 1% dispersion was diluted with 9.9 ml of sterile water to prepare a 0.1% dispersion and the same tests run, the percent reduction in bacteria count was 99.9997% at the 30-second contact time.

Example 4

A 1% dispersion of the compound described in Experiment 1 was prepared by adding 1 gm. of the white solid that had been in storage in a plastic container for over 5 years with 99 gm. of distilled water. The pH was 6. This dispersion was then tested against *Staphylococcus aureus* ATCC 6538 in the manner described in Experiment 2. After 30 seconds of contact time, the percent reduction of the test bacteria was >99.9997%.

Example 5

The 1% dispersion described in Example 3 was contacted with the Gram-negative bacteria *Escherichia coli* 8739 and *Pseudomonas aeruginosa* 15442 each in the manner described in Example 2. After 30 seconds of contact time, the reductions of the test bacteria were 99.9996% and 99.995% respectively.

Example 6

The same dispersion used in Examples 4 and 5 was tested against Gram-positive *Enterococcus faecalis* 29212 in the manner described in Example 2. After 30 second contact time, the bacterial reduction was >99.9986%.

Example 7

A 2% dispersion of the compound ammonium di-nonanoate described in Example 1 was prepared by adding 20 gm. of the white solid to 980 ml. of distilled water with agitation until a solid free emulsion was obtained. This was tested in the AOAC International Use-Dilution Method, the standard for evaluating liquid and dilutable. liquid disinfectants for hard surfaces. The test bacteria was the Gram-negative bacteria *Salmonella enterica* ATCC 10708. In this test, 60 sterilized steel penicylinders are inoculated by soaking in a test culture of the bacteria. The cylinders are then dried in an incubator. After drying, they are submerged in test tubes containing the test substance and allowed to incubate for ten minutes. They are then aseptically transferred to individual tubes containing neutralization/growth medium. The neutralization/growth medium tubes are shaken and incubated. After the incubation period, tubes are qualitatively assessed for growth of the test organism. Tubes demonstrating growth are confirmed to be the test organism by assay on selective media. Results are reported based on the number of tubes demonstrating positive growth within a set of tubes. AOAC International has defined the passing criteria for this test as a disinfectant to be less than or equal to 1 positive carrier out of 60 for *Salmonella enterica*. The number of positive test tubes with the 2% dispersion described above was 0, a pass.

Example 8

To 26.3 gm. of 40% ammonium nonanoate in a liter beaker was added 9.5 gm. of nonanoic acid. A thick gel occurred. To this was added 964 gm. of distilled water with stirring and standing until a uniform milk-like mixture was obtained. The mixture that formed was identical in all respects to the 2% water dispersion described in Example 7.

Example 9

A comparison test for disinfectant properties was made between ammonium di-nonanoate and ammonium nonanoate, the active ingredient in U.S. Pat. No. 9,980,490. A solution of 2.5% ammonium nonanoate was tested in the AOAC International Use-Dilution Method as described in Example 7. Results are reported on the number of tubes demonstrating positive growth within a set of tubes. AOAC has defined the passing criteria for this test as a disinfectant to be less than or equal to 3 positive carriers out of 60 when testing against *S. aureous*. The number of confirmed positive test tubes with the 2.5% ammonium nonanoate was 60, clearly demonstrating no disinfectant properties versus the passing results in Example 7 for ammonium di-nonanoate.

Example 10

One mole (144 g) of liquid octanoic acid was added to 60.7 g of 28% aqueous ammonia in 200 ml of distilled water with stirring. There was a temperature increase due to the heat of neutralization. A clear solution was obtained that foamed on stirring or shaking. The measured pH was 8. The solution was poured into a shallow weighed tray and exposed to the air at room temperature until there was no weight loss (about two weeks). The residue was a white microcrystalline solid that weighed 148.5 g, a yield of 97.4% of a compound with the above formula where X=6 or by the name ammonium di-octanoate. It had little odor. The melting range was 56-58° C. The average elemental analyses of duplicate samples were 4.66% nitrogen, 11.55% hydrogen and 63.21% carbon. This corresponds to a formula of $[CH_3(CH_2)_6COOH]_2NH_3$ with calculated values of 4.65% N, 10.5% H and 62.9% C.

Example 11

A 1% dispersion of the compound described in Example 8 was prepared by adding 1 gm. of the white solid to 99 gm. of distilled water with stirring. The pH of the opaque dispersion was 6. It was then tested against *Staphylococcus aureus* ATCC 6538 in the manner described in Experiment 3. After 30 seconds of contact time, the percent reduction of the test bacteria was >99.629%.

Example 12

One-half mole (86 g) of decanoic acid was dissolved in aqueous ammonia to produce a clear, colorless solution of ammonium decanoate. The measured pH with pH paper was 8. It was allowed to evaporate at room temperature as described in Example 6 for ammonium octanoate. A dry white solid residue weighing 90 g was obtained, a yield of 100% of the X=8 compound (ammonium di-decanaoate). The melting point range of this compound was 68-70° C. The average elemental analyses of duplicate samples were 3.98% nitrogen, 11.96% hydrogen and 66.85% carbon. This corresponds to a formula of $[CH_3(CH_2)_8COOH]_2NH_3$ with calculated values of 3.88% N, 11.08% H and 66.5% C.

Example 13

A 0.5% dispersion of the compound described in Example 10 was prepared by adding 0.5 gm. of the white solid with 99.5 gm. of distilled water. The pH of the dispersion was 6. It was then tested against *Staphylococcus aureus* ATCC 6538 in the manner described in Experiment 3. After 30 seconds of contact time, the percent reduction of the test bacteria was >99.988%.

Example 14

To demonstrate the rheopectic properties of the fatty acid-ammonia complexes in water, 0.5 g of the solid nonanoic acid-ammonium nonanoate compound described in Example I was added to 5 ml of distilled water in a small, narrow, capped vial and stirred with a glass rod until a uniform liquid mixture was obtained. The liquid mixture could be poured back and forth in the vial like any liquid by tilting the vial. The capped vial was then shaken vigorously. The liquid turned into a solid paste-like gel that clung to the sides of the vial. On standing overnight, the gel reverted back to the original liquid form. On shaking again, the gel reformed and again returned to a liquid on standing overnight. This could be repeated again and again with exactly the same results, clearly demonstrating that the complex-water mixtures are rheopectic.

The compounds described herein as disinfectants can be used in combination with each other in any possible ratio.

What is claimed is:

1. A stable, non-hygroscopic water-insoluble compound of the structural formula:

wherein x is from 6 to 8.

2. The stable, non-hygroscopic water-insoluble compound of claim 1 wherein both occurrences of x are the same.

3. The stable, non-hygroscopic water-insoluble compound of claim 1 wherein both occurrences of x are 6.

4. The stable, non-hygroscopic water-insoluble compound of claim 1 wherein both occurrences of x are 7.

5. The stable, non-hygroscopic water-insoluble compound of claim 1 wherein both occurrences of x are 8.

6. The compound of claim 1 wherein the stable, non-hygroscopic water-insoluble compound is formed by hydrogen bonding of a hydrogen atom covalently bonded to nitrogen and an oxygen atom of a carboxylic acid.

7. An aqueous dispersion containing the water-insoluble compound of claim 1.

8. A rheopectic composition comprising the water insoluble compound of claim 1 dispersed in water.

9. The rheopectic composition of claim 8 having a pH less than 7.0.

10. The rheopectic composition of claim 9 having a pH of 6.

11. The rheopectic composition of claim 8 comprising between about 0.1 to about 6 weight percent of the dispersed water insoluble compound.

12. The rheopectic aqueous composition of claim 11 comprising between about 0.5 to about 5 weight percent of the dispersed water insoluble compound.

13. The rheopectic aqueous composition of claim 12 comprising between about 1 to about 2 weight percent of the dispersed water insoluble compound.

14. The rheopectic composition of claim 13 having a pH of 6.

15. The rheopectic composition of claim 8 wherein both occurrences of x are the same.

16. The rheopectic composition of claim 8 which is free of emulsifiers, dispersing agents and suspending agents.

17. The rheopectic composition of claim 8 which is free of surfactants, soaps and wetting agents.

18. A non-hygroscopic, crystalline water-insoluble compound of the structural formula:

$$CH_3(CH_2)_7COOH \cdot CH_3(CH_2)_7COO^-NH_4^+.$$

19. The non-hygroscopic, crystalline water-insoluble compound of claim 18 having a melting point of 62° C.

20. An aqueous rheopectic composition comprising a dispersion of the non-hygroscopic crystalline water-insoluble compound of claim 18 and wherein the pH of the rheopectic composition is 6 and further wherein the amount of the non-hygroscopic, crystalline water-insoluble compound in the aqueous rheopectic composition is from about 0.1 to about 6 weight percent.

* * * * *